(12) United States Patent
Vallana et al.

(10) Patent No.: US 6,451,049 B2
(45) Date of Patent: *Sep. 17, 2002

(54) STENTS FOR ANGIOPLASTY (75) Inventors: Franco Vallana, Turin; Giovanni Rolando, Chivasso; Maria Curcio, Saluggia; Paolo Gaschino, Chivasso, all of (IT)

(73) Assignee: Sorin Biomedica Cardio, S.p.A. (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/410,303

(22) Filed: Oct. 1, 1999

Related U.S. Application Data (63) Continuation-in-part of application No. 09/069,425, filed on Apr. 29, 1998, now Pat. No. 6,325,821.

(51) Int. Cl.[7] .................................................. A61F 2/06
(52) U.S. Cl. ...................................... 623/1.15; 623/1.16
(58) Field of Search ............................... 623/1.11, 1.12, 623/1.13, 1.14, 1.15, 1.16, 1.17, 1.18, 1.19, 1.2, 1.21, 1.22; 606/108, 191, 194, 195, 198

(56) References Cited

U.S. PATENT DOCUMENTS

| 4,503,569 A | 3/1985 | Dotter |
| 4,768,507 A | 9/1988 | Fischell et al. |
| 4,776,337 A | 10/1988 | Palmaz |
| 4,800,882 A | 1/1989 | Gianturco |

(List continued on next page.)

FOREIGN PATENT DOCUMENTS

| DE | 297 01 758 U1 | 5/1997 |
| DE | 297 02 671 I1 | 5/1997 |
| DE | 297 16 476 U1 | 2/1998 |

(List continued on next page.)

OTHER PUBLICATIONS

European Search Report on European Patent Application No. EP 98 10 7382, including annex, dated Sep. 7, 1998, 3 pages.

English language abstract of Italian Patent Application No. TO96A000655.

Topol (ed.), "Coronary Stenting", *Textbook of Interventional Cardiology*, 2(2):687–815 (1994).

*Primary Examiner*—Henry J. Recla
*Assistant Examiner*—Vy Q. Bui
(74) *Attorney, Agent, or Firm*—Popovich & Wiles, P.A.

(57) ABSTRACT

This invention is a stent having a substantially tubular body defining a longitudinal axis comprising first and second adjacent annular segments, each segment defining a substantially sinusoidal shape having a plurality of peaks and valleys, the peaks of the first segment extending toward the second segment and being aligned longitudinally with the valleys of the second segment. The stent has a plurality of bridge elements having a U-shaped portion between first and second connector arms, the first connector arm of one bridge element being connected between a first peak and a first valley of the first segment and the second connector arm being connected between a first peak and a first valley of the second segment in a manner such that the U-shaped portion extends in the direction of the first peak of the first segment and the first valley of the second segment. The bridge elements may be connected to the segments at points spaced 360° apart along the sinusoidal shape of the segments. The segments and bridge elements are configured such that when compression, flexure, and torsion forces are applied to the stent they generate first maximum stress regions, second maximum stress regions and third maximum stress regions which do not overlap.

11 Claims, 8 Drawing Sheets

U.S. PATENT DOCUMENTS

| | | | |
|---|---|---|---|
| 4,830,003 | A | 5/1989 | Wolff et al. |
| 4,856,516 | A | 8/1989 | Hillstead |
| 4,886,062 | A | 12/1989 | Wiktor |
| 4,907,336 | A | 3/1990 | Gianturco |
| 5,421,955 | A | 6/1995 | Lau et al. |
| 5,449,373 | A | 9/1995 | Pinchasik et al. |
| 5,514,154 | A | 5/1996 | Lau et al. |
| 5,569,295 | A | 10/1996 | Lam |
| 5,591,197 | A | 1/1997 | Orth et al. |
| 5,603,721 | A | 2/1997 | Lau et al. |
| 5,649,952 | A | 7/1997 | Lam |
| 5,681,346 | A | 10/1997 | Orth et al. |
| 5,695,516 | A | 12/1997 | Fischell et al. |
| 5,697,971 | A | 12/1997 | Fischell et al. |
| 5,718,713 | A | 2/1998 | Frantzen |
| 5,725,572 | A | 3/1998 | Lam et al. |
| 5,728,131 | A | 3/1998 | Frantzen et al. |
| 5,728,158 | A | 3/1998 | Lau et al. |
| 5,733,303 | A | 3/1998 | Israel et al. |
| 5,733,330 | A | 3/1998 | Cox |
| 5,735,893 | A | 4/1998 | Lau et al. |
| 5,741,327 | A | 4/1998 | Frantzen |
| 5,755,776 | A | 5/1998 | Al-Saadon |
| 5,755,781 | A | 5/1998 | Jayaraman |
| 5,759,174 | A | 6/1998 | Fischell et al. |
| 5,759,192 | A | 6/1998 | Saunders |
| 5,766,238 | A | 6/1998 | Lau et al. |
| 5,766,239 | A | 6/1998 | Cox |
| 5,769,887 | A | 6/1998 | Brown et al. |
| 5,776,161 | A | 7/1998 | Globerman |
| 5,776,183 | A | 7/1998 | Kanesaka et al. |
| 5,807,404 | A * | 9/1998 | Richter .................... 623/1 |
| 5,913,895 | A | 6/1999 | Burpee et al. |
| 5,938,697 | A | 8/1999 | Killion et al. |
| 6,027,526 | A | 2/2000 | Limon |

FOREIGN PATENT DOCUMENTS

| | | |
|---|---|---|
| EP | 0 201 466 | 11/1986 |
| EP | 0 806 190 A1 | 11/1997 |
| EP | 0 873 729 A2 | 10/1998 |
| EP | 0 875 215 A1 | 11/1998 |
| FR | 2 764 794 | 12/1998 |
| IT | TO96A000655 | 7/1996 |
| WO | WO 96/03092 A1 | 2/1996 |
| WO | WO 98/22519 | 5/1998 |
| WO | WO 98/30172 | 7/1998 |
| WO | WO 98/58600 | 12/1998 |
| WO | WO 99/15108 | 4/1999 |
| WO | WO 00/02502 | 1/2000 |
| WO | WO 00/06051 | 2/2000 |
| WO | WO 01/00112 A1 | 1/2001 |

* cited by examiner

STENTS FOR ANGIOPLASTY

This application is a continuation-in-part of Ser. No. 09/069,425, filed Apr. 29, 1998, now U.S. Pat. No. 6,325,821.

FIELD OF THE INVENTION

The present invention relates to stents for angioplasty. In particular, the invention relates to a stent having a cellular design.

BACKGROUND OF THE INVENTION

The term "stent" is intended to indicate devices useful for endoluminal insertion (for example, in a blood vessel), usually effected by means of catheterization, with subsequent deployment in place so as to achieve local support of the lumen. The primary purpose of the stent is to eliminate and avoid the restenosis (i.e., narrowing or closure) of the treated area.

For a general review of vascular stents, reference is made to "Textbook of Interventional Cardiology" edited by Eric J Topol, W.B. Saunders Company, 1994 and, in particular, to section IV of volume II, entitled "Coronary Stenting".

Many patents also provide a general review of stents, for example, U.S. Pat. Nos. 4,503,569; 4,768,507; 4,776,337; 4,800,882; 4,830,003; 4,856,516; 4,886,062; 4,907,336; and EP 0 201 466A.

Notwithstanding the extensive research and experimentation in the stent field, as documented in the patent literature, only a relatively small number of operative solutions have, until now, found practical application. This is due to various factors, which include the following problems or requirements:

- while moving toward the treatment site, the stent should be capable of adapting to the path, which may include various curved sections;
- distortion of the stent while it is being positioned should not be detrimental to the ability of the stent to provide an effective support when it is positioned and deployed;
- the longitudinal shortening effect which occurs in many stents upon deployment should be limited, if not avoided;
- maximum homogeneity and uniformity in the expansion of the stent should be achieved at the desired location;
- an extensive support surface should be provided to the wall of the lumen which is being supported;
- the origination of complex shapes and/or possible stagnation sites, especially in blood vessels, should be avoided, in order to avoid undesirable phenomena such as coagulation or thrombosis; and
- the stents should be able to be simply and reliably produced using available technology and they should incorporate the requirements listed above.

A stent is subject to various forces, including compression, flexure, and torsion. These stresses often cause the stent to perform in an undesirable manner. Additionally, a significant disadvantage of current stent designs is their failure to distribute these stresses throughout the structure of the stent. Each of these stresses is maximized in a particular area of the stent. In current stent designs two or more of these areas of maximum stress overlap. This results in at least two problems. First, an overlap of the maximum stress areas may overly fatigue the stent and cause failure in an area of overlapped maximum stress. Second, the failure to distribute or discharge the maximum stress of these forces at different areas causes stress concentration on the vessel wall which may cause vessel wall injury. Thus what is needed in the art is a stent meeting the requirements listed above that will avoid stress concentration and elastic distortion as well as provide good elastic matching between the stent and the vessel into which it is placed.

SUMMARY OF THE INVENTION

This invention is a stent having a substantially tubular body defining a longitudinal axis comprising first and second adjacent annular segments, each segment defining a substantially sinusoidal shape having a plurality of peaks and valleys, the peaks of the first segment extending toward the second segment and being aligned longitudinally with the valleys of the second segment; a plurality of bridge elements having a U-shaped portion between first and second connector arms, the first connector arm of one bridge element being connected between a first peak and a first valley of the first segment and the second connector arm being connected between a first peak and a first valley of the second segment in a manner such that the U-shaped portion extends in the direction of the first peak of the first segment and the first valley of the second segment.

The U-shaped portion of the plurality of bridge elements may be oriented in the same direction. Alternately, they may be oriented in one direction between one pair of adjacent annular segments, and in the opposite direction between another pair of adjacent annular segments. Preferably, the connector arm of the bridge element joins the annular segment at the zero point of the sinusoidal wave shape. In one embodiment, each connector arm joins each annular segment at zero points of the sinusoidal wave separated by 360°. Alternately, the connector arms may join zero points separated by 360° between one pair of adjacent segments, and zero points separated by 720° between another pair of adjacent segments.

In a second aspect, this invention is a method of preventing restenosis by providing the stent described above and deploying it within a body lumen.

In a third aspect, this invention is a method of making a stent by providing a tubular blank and forming the tubular blank into a stent having the geometry described above.

In a further aspect this invention is a stent having a substantially tubular body defining a longitudinal axis. The stent comprises first and second adjacent annular segments, each segment having a substantially sinusoidal wave shape. The stent further includes first and second bridge elements, the first bridge element having a first end connected to the first annular segment at a zero point of the sinusoidal wave shape and having a second end connected to the second annular segment at a zero point of the sinusoidal wave shape. The second bridge element has a first end connected to the first annular segment at a zero point of the sinusoidal wave shape spaced 360° from the connection of the first bridge element to the first annular segment and a second end connected to the second annular segment at a zero point of the sinusoidal wave shape 360° from the connection of the first bridge element to the second segment, the first and second bridge elements and a portion of the first and second annular segments between the connection points of the bridge elements together defining a cell.

In a further aspect, the invention is a stent having a substantially tubular body defining a longitudinal axis and having a plurality of annular segments, each segment having a substantially sinusoidal wave shape. The stent includes a plurality of bridge elements, each bridge element having a first end connected to one annular segment at a zero point of the sinusoidal wave shape and a second end connected to an annular segment adjacent to the one annular segment at a zero point of the sinusoidal wave shape of the adjacent annular segment, the annular segments and bridge elements being configured such that when compression, flexure and torsion forces are applied to the stent they generate first maximum stress regions, second maximum stress regions, and third maximum stress regions, where the first, second and third maximum stress regions do not overlap.

BRIEF DESCRIPTION OF THE DRAWINGS

The invention will now be described with reference to the accompanying drawings.

FIG. 3(a) illustrates an expanded view of a single cell within the wall of the stent of FIG. 2 and FIGS. 3(b), 3(c), 3(d), 3(e) and 3(f) show the cross-sectional areas of portions of the stent.

DETAILED DESCRIPTION OF THE PREFERRED EMBODIMENTS

A stent is inserted into a lumen, such as a blood vessel, at a site where stenosis, i.e., narrowing or stricture, is to be corrected. The stent is a tubular envelope, tubular body, or cylinder having apertured walls, such as, for example, a mesh-like structure. The stent typically has dimensions between several millimeters and several tens of millimeters in length, and a wall thickness of the order of, for example, several hundredths of millimeters. The stent is normally positioned in situ by catheterization through the vasculature followed by radial expansion from an introduction diameter of, for example, about 1.0 to 1.5 mm, to an expanded diameter of, for example, about 3 to 4 mm. In this expanded condition, the stent exerts a supporting force on the lumen, thereby avoiding or at least slowing restenosis of the vessel. In general, the external diameter of the stent in the radially-contracted condition is chosen to enable the introduction of the stent into a lumen, while the expanded diameter corresponds to the diameter required to be maintained in the lumen once the stenosis has been eliminated. It should also be remembered that, although the principle application of the stent described is in relation to the treatment of blood vessels, it may also be useful as a support element for any lumen present in the human or animal body.

The stent of this invention is a tubular body, i.e., a cylinder, with an open, or apertured, mesh-like structure. The stent is capable of being dilated from a radially-contracted position to a radially-expanded position. The tubular body is comprised of a wall having an inner surface and an outer surface defining a radial stent thickness therebetween. In one embodiment, the material making up the mesh-like structure of the stent varies in its cross-sectional shape and/or cross-sectional area. It has been discovered that this cross-sectional variation (and thus a variation in thickness and/or width in the stent wall) produces a particularly desirable stent because the strength, flexibility, and support of the stent may be varied in localized areas. In areas requiring flexibility, the width as measured along the circumference of the tubular body and/or the radial thickness are made smaller to enhance flexibility. In areas requiring strength, the width and/or thickness are made larger. In areas not requiring flexibility, the width is increased to provide added vascular support.

In the embodiments illustrated in the Figures, the stent is shown in planar views so that the geometry of the stent may be seen easily. The body of the stent extends longitudinally in the direction identified as the Z axis. It also lies in the Z plane, i.e., a plane coincident with the Z axis. During delivery and use of the stent, the stent may be flexed, bent or folded; thus good flexibility is one of the required characteristics of the stent. Another important characteristic of both the design and the material of the stent includes strength, i.e., the ability to withstand stresses due to compression, flexure, and torsion, as discussed further below.

Figure 1:
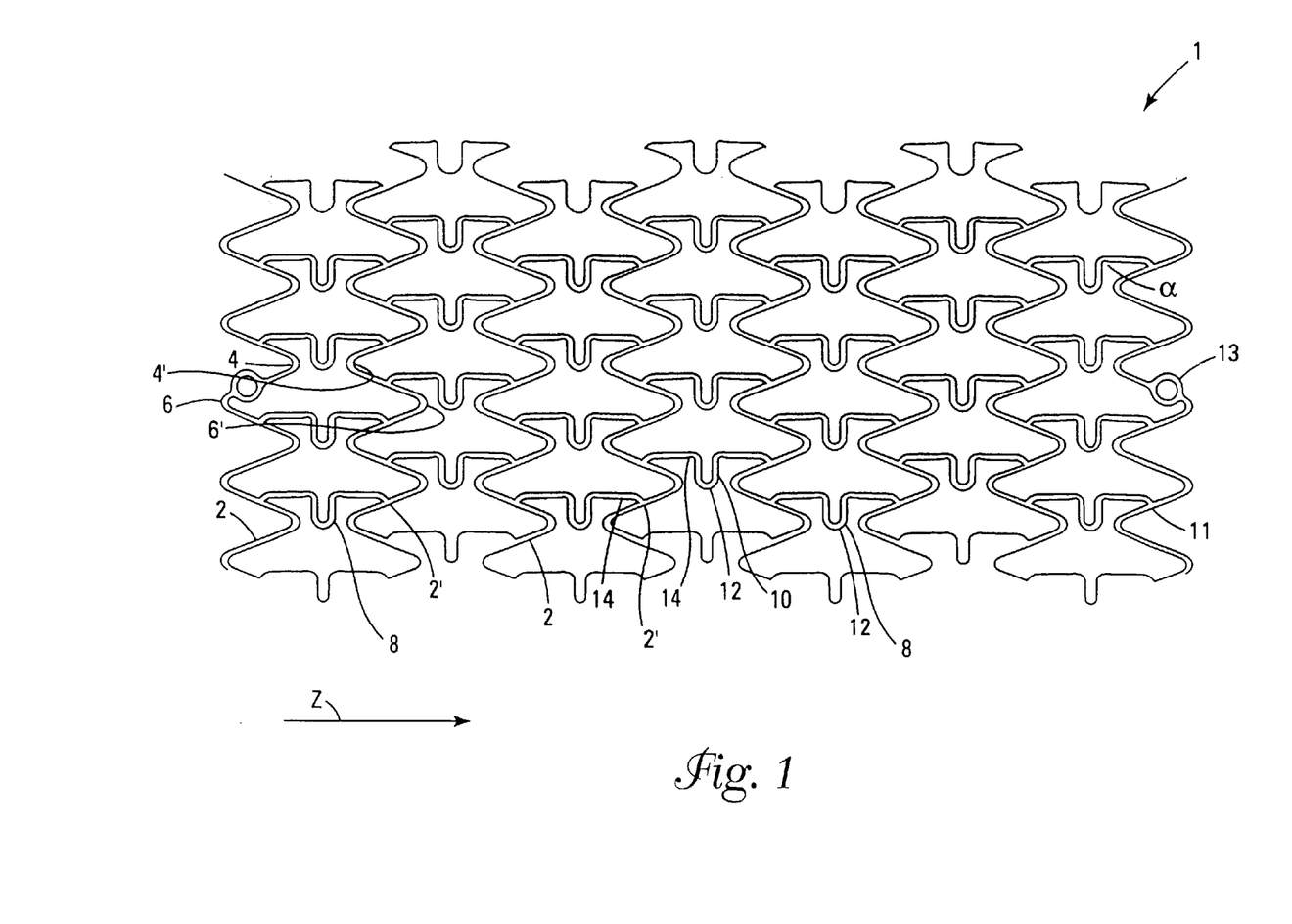
FIG. 1 is a plan view of the tubular stent of the present invention cut longitudinally and opened to lie within a single plane, the stent being in a radially contracted configuration.

FIG. 1 illustrates a plan view of the stent of this invention. The body of stent 1 is comprised of a plurality of successive segments 2 of generally annular form. FIG. 1 shows a stent comprising eight annular segments 2. Typically, the length of segments 2 measured in the longitudinal direction (i.e., along the Z axis) may range up to several millimeters (mm) but preferably is approximately 2 mm. That is, segments 2 are fairly "short" in comparison to the total length of the stent.

The various segments of stent 1 are joined together by bridge elements 8 (which are actually integral components of the stent wall) that connect adjacent segments 2 and enable stent 1 to flex or bend.

Radiopaque marker 13 optionally is provided. Marker 13 is integral with segments 2 and typically is located on the proximal and/or distal ends of the stent. "Proximal and distal ends" refers to the portion of the stent nearest and farthest, respectively, from the point of entry of the stent into the vasculature. Suitable radiopaque markers include metals such as platinum, tantalum, gold, and alloys of these metals. Such markers permit exact placement of a stent within the vasculature of a patient. During manufacture the radiopaque marker may be crimped into a hole in the stent wall.

The longitudinal flexibility of stent 1, necessary to assist in its delivery and location at the implantation site, is essentially due to bridge elements 8, while its structural strength, that is, its support of the lumen, is due primarily to the structure of segments 2. The desired characteristics of the stent can be obtained by adapting the arrangement and relationship of the bridge elements and the segments.

FIG. 1 shows a plan view of a stent which has been cut open and laid flat; that is, the stent is no longer in a tubular shape. FIG. 1 illustrates that each segment 2 has a serpentine or sinusoidal wave shape. Each segment comprises peaks 4 and valleys 6. Each annular segment is a mirror image of an adjacent annular segment about a plane perpendicular to the longitudinal axis of the stent. Thus, the peaks of one segment are aligned longitudinally with valleys of an adjacent segment. For purposes of this description the term "sinusoidal wave shape" means that the annular segments have an undulating repeating pattern similar to that of a sine wave. It is not intended to mean that the shape is limited to that of a sine wave.

Figure 2:
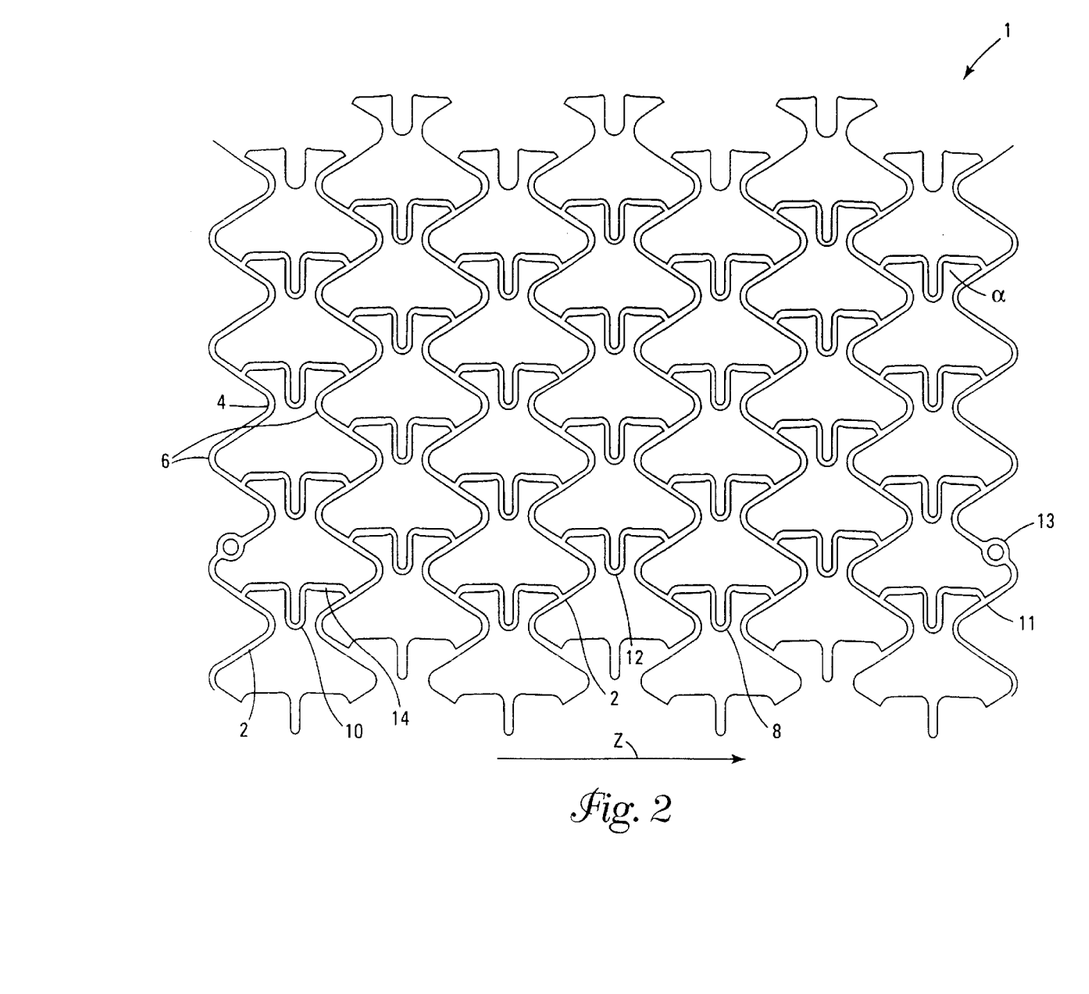
FIG. 2 illustrates the stent of FIG. 1 in its radially expanded configuration.

Bridge elements 8 separate adjacent segments and maintain a distance between them in both the expanded and contracted conditions. Each bridge element 8 comprises a concave portion, or U-shape 10, having apex 12. The U-shape is adjoined to two connector arms 14 which extend from the U-shape and adjoin adjacent sinusoidal-shaped segments 2 at a zero point of the sinusoidal wave shape of each segment. The point of connection is between a peak and a valley of each segment such that the apex of the U-shape extends in the direction of the converging peak and valley that is nearest the attachment of the connector arm. These arms extend away from the U-shape and curve back to join the segments in the direction of the apex of the U-shape. Preferably these arms form an angle a of about 90 degrees with the U-shape. Bridge elements 8 are relatively flexible and change shape only slightly from the contracted to the expanded condition, as can be seen in FIGS. 1 and 2. Arms 14 adjoin adjacent sinusoidal wave shaped segments between a peak and a valley and preferably at zero-point 11 of the sinusoidal shape. (On a sine curve plotted on an X and Y axis, the "zero-point" is that point that intersects the X axis.)

FIGS. 1 and 2 illustrate an embodiment of the stent of this invention wherein the connector arms of each bridge element adjoin alternate zero points of each adjacent segment. That is, in terms of the sinusoidal wave shape of each segment, bridge elements are connected at zero points separated by 360°. This results in even spacing of bridge elements between adjacent segments. In addition, the bridge elements are oriented in the same direction; that is, the U-shaped portion of each bridge element faces the same direction. It has been found that connection of the bridge elements at the zero points not only produces a very elastic joint but also results in the longitudinal length of the stent being the same in the contracted condition and the expanded condition and in all degrees of expansion therebetween.

A radially-contracted condition of the stent is illustrated in FIG. 1. This condition is slightly expanded from the stents fully contracted delivery condition so that the details of the stents structure may be more clearly shown. The radially-expanded condition of the stent shown in FIG. 2. FIG. 2 shows that a segment 2 is elongated compared to the same segment in FIG. 1. That is, the segments retain the sinusoidal shape, but the amplitude and the frequency of the sine wave is less in the expanded condition than in the contracted condition. FIGS. 1 and 2 also show that the connector arms 14 remain substantially parallel to the longitudinal axis of the stent in both the radially contracted position (FIG. 1) and radially expanded position (FIG. 2).

Figures 3A, 3B, 3C, 3F:
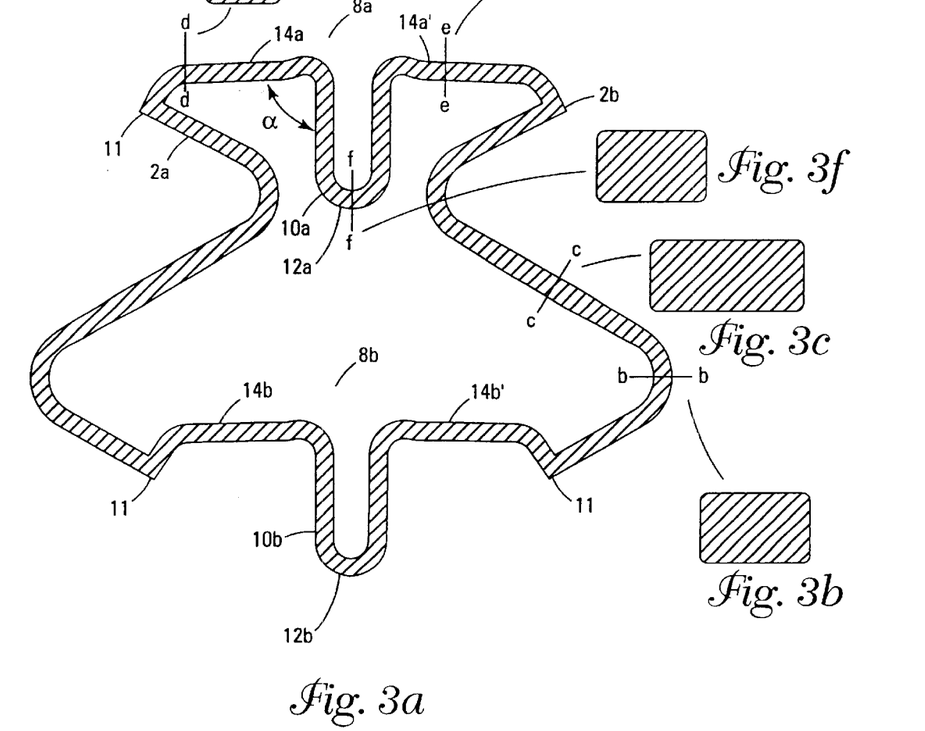
Figure 3D:
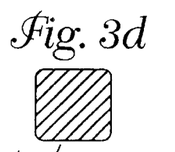
Figure 3E:
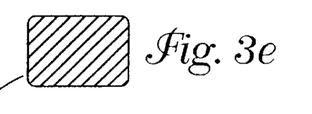

An alternative way of describing the structure of the stents of this invention is in terms of its substantially tubular surface which includes multiple cells. FIG. 3(a), is a view of one cell of the stent of FIG. 2. FIGS. 1 and 2 illustrate that the stent is made up of individual, interconnected cells, each cell having the same size and shape. FIGS. 3(b) to 3(f) illustrate that the cross sectional shape and area of the material making up the stent varies over the cell. The perimeter of a cell is formed from portions of adjacent sinusoidal segments (2a and 2b) and two bridge elements (8a and 8b). Sinusoidal segment portions 2a and 2b are 360° portions of the sinusoidal wave shape of the annular segments. Arms 14a and 14a' extend from U-shape portion 10a of bridge element 8a. Apex 12a of bridge 8a is oriented in the same direction as apex 12b of bridge 8b. Bridges 8a and 8b adjoin adjacent segments 2a and 2b at zero points 11 of the sinusoidal shape; that is, between the peaks and valleys of the segments. Bridge element 8b, having U-shape 10b, apex 12b, and arms 14b and 14b', forms the remainder of the cell.

FIGS. 3(b), 3(c), 3(d), 3(e) and 3(f) show the shape and size of the cross-section of different portions of the cell taken along lines b—b, c—c, d—d, e—e and f—f respectively. It is preferred that the cross-sectional area of the material making up the stent vary. The cross-sectional shape may vary as well. An alternate way of describing this is that the width of the material making up the stent of FIGS. 1 and 2 (i.e., the width of any portion of a bridge or a sinusoidal segment in plane Z) may be different than the thickness of that portion (i.e., the dimension in a plane X, perpendicular to plane Z). It has been found that varying the cross-sectional area of different portions of the material of the stent produces optimum strength, flexibility, and support, enabling the stent to accommodate the differing stresses it encounters during use.

Through the use of stress analysis of the stent, it has been determined that during use, different areas of the cells are stressed, depending upon the forces acting on the stent. For example, when the stent is under compression, stress is maximized in the peaks and valleys of the sinusoidal segments. When the stent is flexed, the stress is maximized around the apex of the U-shape of the bridge elements. Under torsion, the stress is maximized at the ends of the connector arms of the bridge elements, i.e., where a bridge element connects to a sinusoidal segment.

Figure 4A:
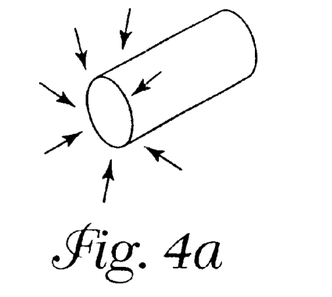
FIGS. 4(a) to 4(f) illustrate the effects of compression, flexure, and torsion, respectively, on a cell of the stent of this invention.
Figure 4B:
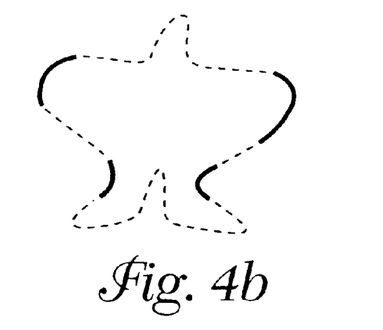
Figure 4C:
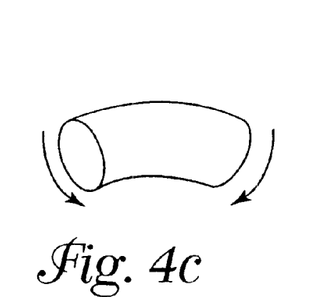
Figure 4D:
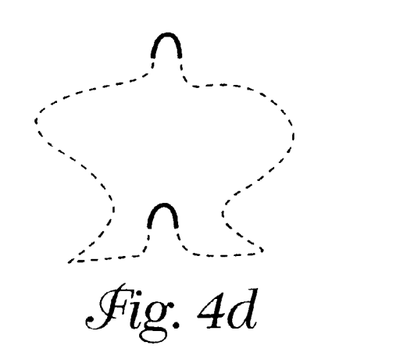
Figure 4E:
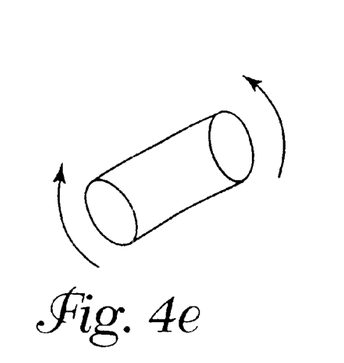
Figure 4F:
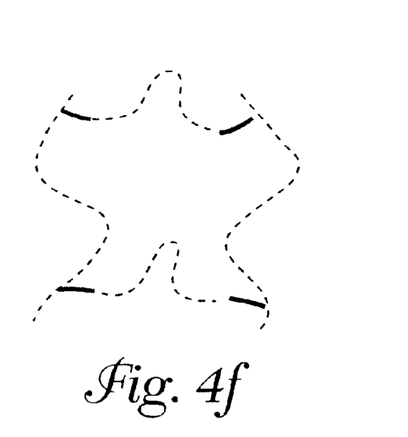

FIGS. 4(a) to 4(f) illustrate the effects of compression, flexure, and torsion, respectively, on one cell of the stent of this invention. The arrows indicate the direction of the forces applied to the stent. The areas of the stent cell having the greatest stress concentration are indicated by solid lines. In FIG. 4(a), the stent is subjected to a compression force. FIG. 4(b) shows that the areas of greatest stress occurs at the peaks and valleys of the sinusoidal shaped segments. FIG. 4(c) shows s stent undergoing flexure. FIG. 4(d) indicates that the areas of greatest stress occur at the apex of the U-shape of the bridge. FIG. 4(e) shows a stent under torsion. FIG. 4(f) indicates that the maximum stress occurs at the areas where the bridge joins the sinusoidal shaped segments, i.e., at the zero point.

It is an advantage of the cellular design of the stent of this invention that the areas of maximum stress induced by compression, flexure and torsion forces do not overlap. This reduces the risk that a particular area of the stent cell structure will be overly fatigued and fail. It also reduces the risk of causing damage to the vessel wall which can result if there is a significant stress concentration at any portion of the cellular structure. In the stent of this invention maximum stresses from compression, flexure and torsion are distributed and discharged over three separate areas of the cellular structure thus reducing the risk of stent failure and damage to vessel walls.

In the stents of this invention, it is possible to alter the thickness and width of various portions of the stent during the manufacturing process. One way to do this is to form the desired wall geometry in a continuous tubular blank and then cut or machine the stent from this blank. For example, techniques such as laser incision, photo-incision, and electroerosion may be used to form a desired geometry. In this way, the stent bridges and sinusoidal segments are formed.

Figure 5A:
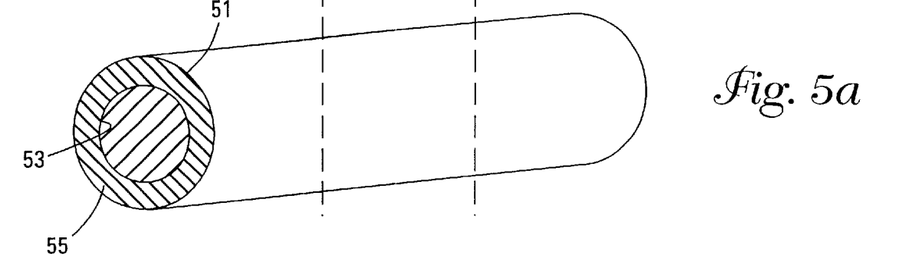
FIGS. 5(a) to 5(f) illustrate various shapes of the wall of a continuous tubular blank used to make the stent of this invention.
Figure 5B:
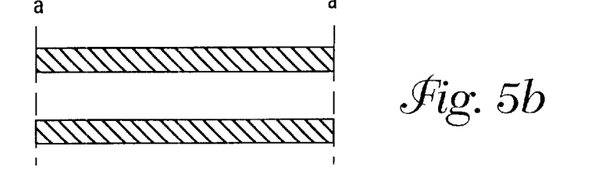
Figure 5C:
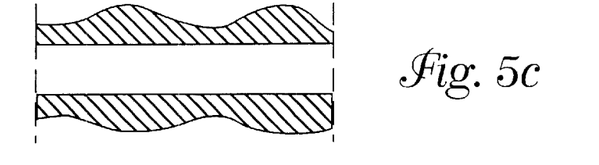
Figure 5D:
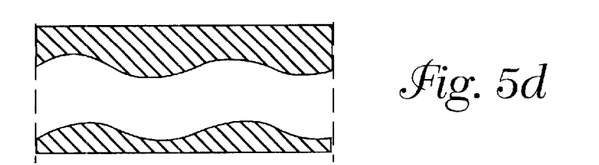
Figure 5E:
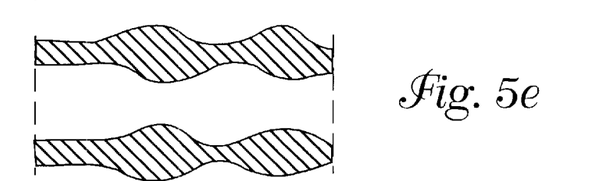
Figure 5F:
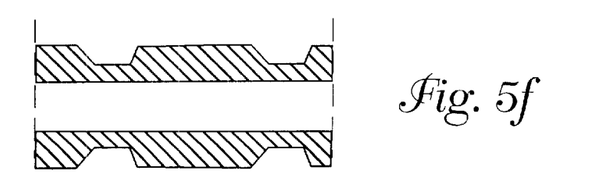

FIG. 5a shows a continuous tubular blank from which stents can be formed. The tubular blank has outer surface 51 forming the outer diameter and inner surface 53 forming the inner diameter; surfaces 51 and 53 are separated by wall thickness 55. The characteristics of the stent including wall thickness and shape can be varied in accordance with the shape and surface configuration of inner and outer surfaces 53 and 51 of the tubular blank. Accordingly, the wall of the stent may be formed so that it has a variety of cross sectional shapes. FIGS. 5(b) to 5(f) show a section or slice of differently shaped tubular blanks between lines a–a' and illustrate various wall shapes. The inner and outer surfaces of the tubular blank may be substantially parallel as in FIG. 5b. This is consistent with the embodiment shown in FIGS. 3(a) to 3(f). Alternatively, the surface configuration of the outer and/or inner surfaces may be varied as in FIGS. 5(c) to 5(f). For example, the inner diameter of the tube may be constant and the outer diameter may vary, as in FIG. 5(c), or the converse, as in FIG. 5(d), may be used. FIGS. 5(e) and 5(f) illustrate tube walls having variable inside and outside diameters. Such tubular blanks are then machined to form the desired stent as described above. The result is that the desired thicknesses and widths can be provided to different portions of the stent.

Figure 6A:
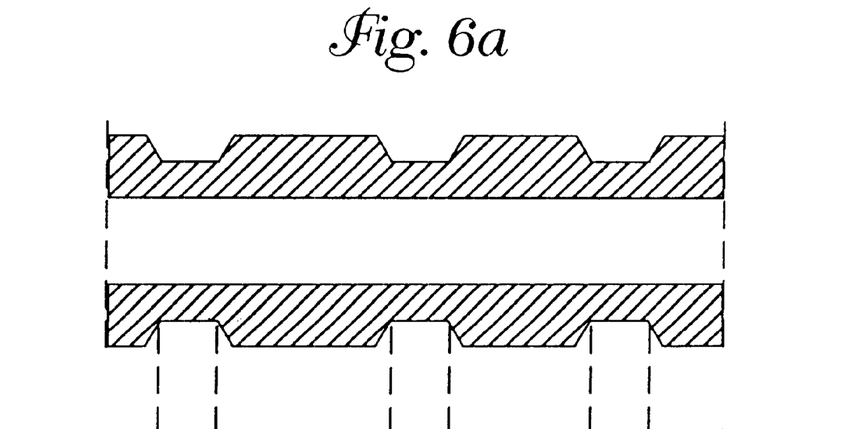
FIGS. 6(a) and 6(b) illustrate the variation in cross section of a section of the stent of this invention.
Figure 6B:
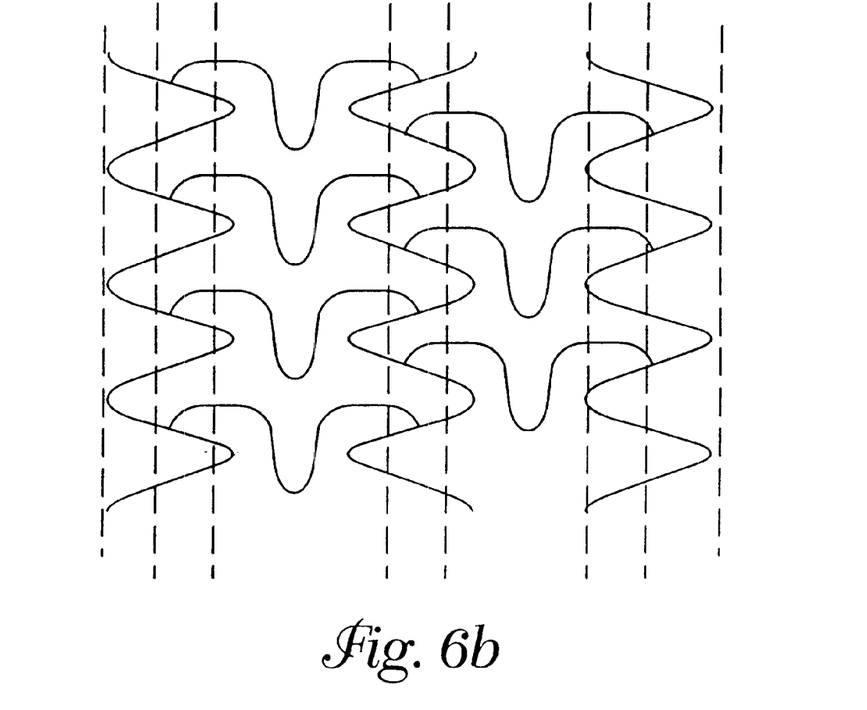

FIGS. 6(a) and 6(b) show a further embodiment of the invention and illustrate how the shape of the wall of a continuous tubular blank corresponds to the stent of this invention. FIG. 6(a) shows a longitudinal cross-section of a portion of a tubular blank having a constant inner diameter but varying outer diameter. This blank is then used to form the sinusoidal segments and bridges of the stent. FIG. 6(b) shows that the regions of the bridges adjoining the sinusoidal shaped segments (i.e., at the zero point) may be made with a smaller thickness than the remaining portions of the stent.

Figure 7:
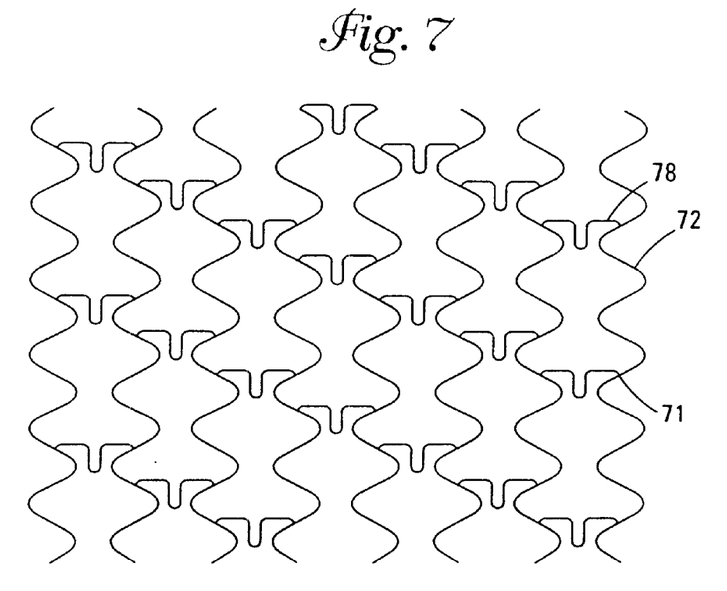
FIG. 7 is a view similar to FIG. 1 of another embodiment of the stent of this invention.

Turning now to FIG. 7, various alternative embodiments of the stent of this invention are illustrated. This stent comprises bridge elements 78 adjoining sinusoidal shaped segments 72 at zero points 71 of the sinusoidal shape. The bridge elements are evenly spaced. In this case the bridge elements are spaced apart 720° along the sinusoidal shape of the segments. The apices of each bridge element face the same direction. As described above, when viewed as a cellular structure, the stent of FIG. 4 illustrates cells all having the same shape and size. In contrast to FIGS. 1 and 2, this stent has fewer connecting bridges and fewer cells.

Figure 8:
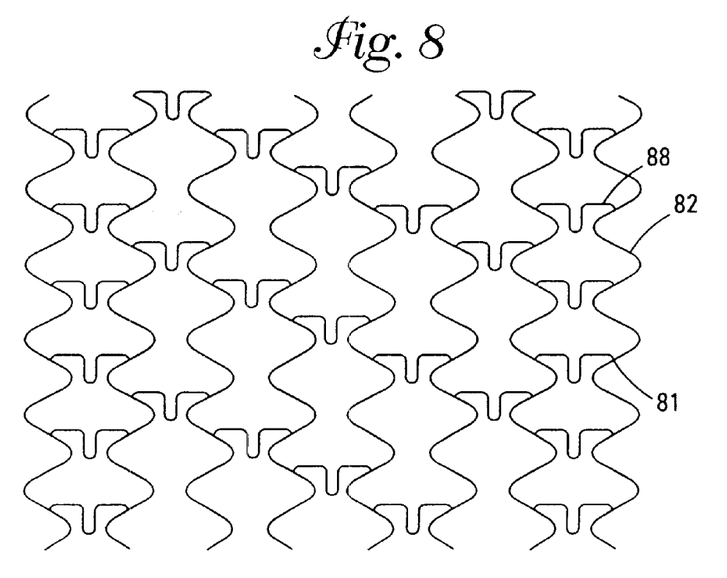
FIG. 8 is a view similar to FIG. 1 of another embodiment of the stent of this invention.

The stent of FIG. 8 is a hybrid of FIGS. 1 and 6. Bridge elements 88 adjoin adjacent segments 82 at zero points 81 of the sinusoidal shape. All bridge elements are oriented similarly (i.e., face the same direction). The bridge elements adjoining adjacent segments are evenly spaced. However, the number and spacing of bridge elements is not the same for each pair of adjacent segments. This results in cells of unequal size and may produce regions of variable flexibility as well as strength. An advantage to having a greater number of bridge elements (and hence cells) at either end of the stent is that they provide additional stability and strength to the ends of the stent while having fewer cells in the middle portion of the stent provides additional flexibility.

Figure 9:
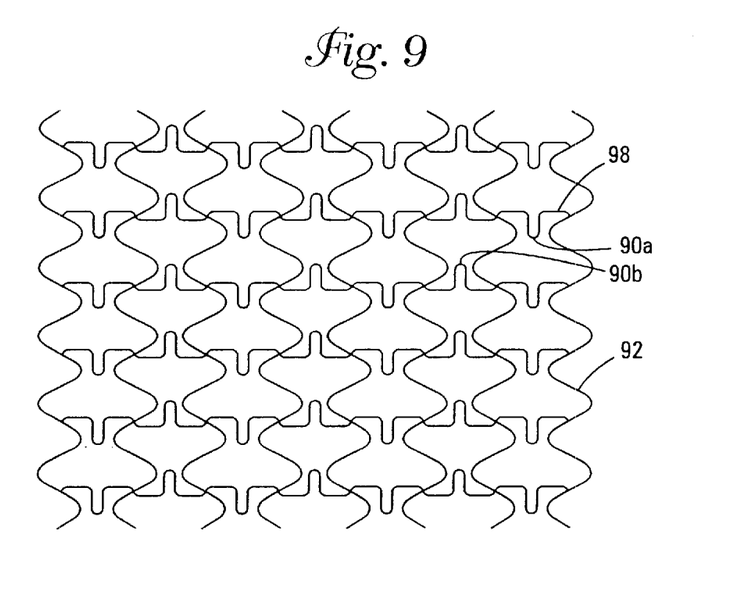
FIG. 9 is a view similar to FIG. 1 of another embodiment of the stent of this invention.

Another variation of the stent is illustrated in FIG. 9. The bridge elements are evenly spaced throughout the stent, forming cells all of equal size and shape. However, apices (for example, 90a and 90b) of bridge elements 98 face opposite directions in adjacent pairs of segments 92.

Figure 10:
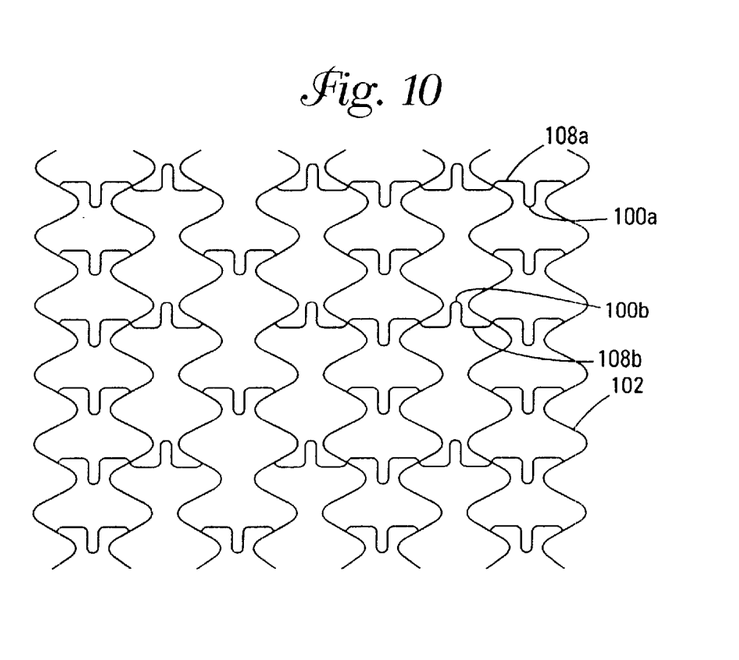
FIG. 10 is a view similar to FIG. 1 of another embodiment of the stent of this invention.

FIG. 10 illustrates yet another variation of the stent, wherein U-shaped portions 100a and 100b of bridge elements 108a and 108b, respectively, are facing in opposite directions in adjacent pairs of segments 102 and wherein the cells formed at each end of the stent are of different size than those of the remaining cells. The bridge elements adjoining any pair of adjacent segments are evenly spaced, but the number and spacing of bridge elements is not the same for each pair of adjacent segments. This results in cells of unequal size, and, in similar fashion to FIG. 8, produces regions of greater strength at either end of the stent.

It is generally preferable to align the bridge elements between adjacent sinusoidal segments with the apices pointing in the direction of a converging peak and valley of the adjacent segments. This configuration provides a number of advantages. One advantage is that, in the expanded configuration, the stent cell structure is sufficiently open to permit access to the lumen. For example, it is possible to manipulate catheters through the stent wall into vessel bifurcations in order to treat those vessels. Another advantage is that the stent geometry provides a smooth profile for delivery when in the contracted position. In the stent design of this invention, the U-shape of the connecting bridges lies between a converging valley and peak of adjacent sinusoidal segments and acts as a bridge therebetween. This reduces the chance of snagging any cellular matter from the inside of the lumen. The peaks or valleys of some prior art stents protrude especially when the stent is bent during delivery. This protruding peak or valley can snag on a vessel wall or plaque, making delivery and positioning of the stent difficult. A further advantage is provided by the configuration of the bridge elements. The connector arms and U-shaped portion of the bridge elements act in cooperation with the segments to provide an effective support surface for the vessel wall while at the same time minimizing the amount of stent material which must be used.

As to deployment (that is, the in situ expansion) of the stent, currently the most widely used method is to use a balloon catheter, disposing the stent about the balloon of the catheter in the contracted condition and then expanding the balloon once the stent has been delivered to the deployment site. Different solutions are also possible, such as using superelastic materials that expand when the stent reaches the implantation site. Typically these materials are held in a contracted condition by means of a containment element that is released when the stent has reached the desired location and position. Materials having a "shape memory" that expand from a first configuration to a second expanded configuration when heated to a transition temperature (i.e., body temperature) also may be used in order to achieve the radial expansion in the implant position.

Usually the stent is made from a metal capable of satisfying two fundamental requirements: the ability to deform during the expansion phase and the ability to resist forces which could lead to contraction of the stent. That is, the stent retains the expanded shape. For example, the stents of this invention may comprise 316 stainless steel or a shape memory material known under the commercial designation "Nitinol". "Nitinol" is a nickel-titanium alloy that has been shown to be successful due to its superelasticity as well as its shape memory. Stents also may comprise biodegradable and/or biocompatible polymers, as known to one of skill in the art.

These technological aspects will not be dealt with in detail in the present description in that they are not in themselves relevant to the comprehension and production of the invention. This also applies essentially to the technology for the production of the stent according to the invention. As described above, the stent of this invention comprises a tubular body with an apertured wall. Methods of making the stent include:

forming the stent from a continuous tubular blank intended to be segmented into individual stents, with the apertured parts being formed using techniques such as laser incision, photo-incision, electroerosion, and the like;

forming the stent from a strip-like body in which the apertured zones are formed, for example, using the techniques listed above, with the subsequent closure of the strip-like element into a tube; and forming the stent from metal wire shaped by the subsequent attachment of wire loops, for example, using operations of micro welding, brazing, gluing, crimping, and the like.

The first arrangement described is the one currently preferred for producing stents of this invention. In particular, the use of laser beams to cut a continuous tubular blank has been shown to be the most flexible way to modify rapidly the characteristics of the stent during production.

Such methods may be used to produce a stent having either constant or variable wall thickness, and, in either case, with wall material having different cross-sections. These methods include making the stent from a continuous tubular blank and machining, grinding, chemically etching, or electron discharge machining the tube to produce the desired pattern and also obtain sections of desired cross-section. Alternatively, a tubular blank having constant or variable thickness down its length could be laser cut to form the desired arrangement of segments and bridges. A stent could be formed and then the inside surface could be turned or micro-etched.

The production method is not critical to the stents of this invention, as they may be formed by any desired method. This applies to the choice of the individual techniques and the order in which the various operations (the production of the apertured parts, segmentation, possible folding of the strip-like element, etc.) are performed.

Although particular embodiments have been disclosed herein in detail, this has been done for purposes of illustration only, and is not intended to be limiting with respect to the scope of the appended claims, which follow. In particular, it is contemplated by the inventor that various substitutions, alterations, and modifications may be made to the invention without departing from the spirit and scope of the invention as defined by the claims. For example, the frequency, number, and location of bridge elements and sinusoidal segments may be varied as necessary to obtain the desired characteristics of the stent.

What is claimed is:

1. A stent having a substantially tubular body defining a longitudinal axis comprising:

first and second adjacent annular segments, each annular segment defining a substantially sinusoidal shape having a plurality of peaks and valleys, the peaks of the first annular segment extending toward the second annular segment and being aligned longitudinally with the valleys of the second annular segment, the valleys of the second annular segment extending toward the first annular segment;

a plurality of bridge elements each having a U-shaped portion between first and second connector arms, the first connector arm of at least one bridge element having a first region connected between a first peak and a first valley of the first annular segment and the second connector arm of the at least one bridge element having a second region connected between a first peak and a first valley of the second annular segment, the at least one bridge element having a third region between the first and second regions, the first region having a first radial thickness, the second region having a second radial thickness, the third region having a third radial thickness, the third radial thickness being greater than either of the first and second radial thicknesses.

2. The stent of claim 1 wherein the first and second connector arms are connected in a manner such that the U-shaped portion extends in the direction of the first peak of the first annular segment and the first valley of the second annular segment.

3. The stent of claim 1 wherein the first peak of the first annular segment is aligned longitudinally with the first valley of the second annular segment and the first valley of the first annular segment is aligned longitudinally with the first peak of the second annular segment.

4. The stent of claim 1 wherein the third region includes the U-shaped portion.

5. The stent of claim 1 further comprising a third annular segment connected to the second annular segment by the plurality of bridge elements, wherein the U-shaped portions of the plurality of bridge elements are oriented in one direction between the first and second annular segments and in the opposite direction between the second and third annular segments.

6. The stent of claim 1 wherein the connector arm of the at least one bridge element joins the first annular segment at a zero point of the sinusoidal shape.

7. The stent of claim 6 wherein each connector arm of the plurality of bridge elements joins the first and second annular segments at a zero point of the sinusoidal shape.

8. The stent of claim 1 further comprising a third annular segment connected by the plurality of bridge elements to the second annular segment, wherein the plurality of bridge elements join zero points separated by 360° between the first and second adjacent segments, and further wherein the bridge elements join zero points separated by 720° between the second and third adjacent segments.

9. A method of preventing restenosis in a vessel comprising:

providing a stent having a substantially tubular body defining a longitudinal axis, the stent comprising first and second adjacent annular segments, each segment defining a substantially sinusoidal shape having a plurality of peaks and valleys, the peaks of the first annular segment extending toward the second annular segment and being aligned longitudinally with the valleys of the second annular segment, the valleys of the second annular segment extending toward the first annular segment such that a first peak of the first annular segment is longitudinally aligned with a first valley of the second annular segment and a first valley of the first annular segment is aligned longitudinally with a second peak of the second annular segment, a plurality of bridge elements having a U-shaped portion between first and second connector arms, the first connector arm of at least one bridge element having a first region connected between the first peak and the first valley of the first annular segment and the second connector arm of the at least one bridge element having a second region connected between the first peak and the first valley of the second annular segment, the at least one bridge element having a third region between the first and second regions, the first region having a first radial thickness, the second region having a second radial thickness, the third region having a third radial thickness, the third radial thickness being greater than either of the first and second radial thicknesses;

advancing the tubular body in the contracted condition through the lumen of the vessel to an area of stenosis; and deploying the tubular body within the lumen of the vessel by expanding the tubular body from the contracted to the expanded condition.

10. The method of claim 9 wherein, in the step of providing the stent, the U-shaped portion extends in the direction of the first peak of the first annular segment and the first valley of the second annular segment.

11. A method of making a stent comprising:

providing a tubular blank defining a longitudinal axis; and forming the blank into first and second adjacent annular segments connected by a plurality of bridge elements, each annular segment defining a substantially sinusoidal shape having a plurality of peaks and valleys, the peaks of the first annular segment extending toward the second annular segment and being aligned longitudinally with the valleys of the second annular segment, the valleys of the second annular segment extending toward the first annular segment such that a first peak of the first annular segment is longitudinally aligned with a first valley of the second annular segment and a first valley of the first annular segment is aligned longitudinally with a second peak of the second annular segment, the plurality of bridge elements having a U-shaped portion between first and second connector arms, the first connector arm of at least one bridge element having a first region connected between the first peak and the first valley of the first annular segment and the second connector arm of the at least one bridge lement having a second region connected between the first peak and the first valley of the second annular segment, the at least one bridge element having a third region between the first and second regions, the first region having a first radial thickness, the second region having a second radial thickness, the third region having a third radial thickness, the third radial thickness being greater than the first and second radial thicknesses.

* * * * *